United States Patent
Ke et al.

(10) Patent No.: US 7,610,086 B1
(45) Date of Patent: Oct. 27, 2009

(54) SYSTEM AND METHOD FOR DETECTING CARDIAC ISCHEMIA IN REAL-TIME USING A PATTERN CLASSIFIER IMPLEMENTED WITHIN AN IMPLANTED MEDICAL DEVICE

(75) Inventors: Chunlei Ke, Stevenson Ranch, CA (US); Jong Gill, Valencia, CA (US); Peter Boileau, Valencia, CA (US)

(73) Assignee: Pacesetter, Inc., Sylmar, CA (US)

( * ) Notice: Subject to any disclaimer, the term of this patent is extended or adjusted under 35 U.S.C. 154(b) by 643 days.

(21) Appl. No.: 11/394,724

(22) Filed: Mar. 31, 2006

(51) Int. Cl.
*A61B 5/04* (2006.01)
(52) U.S. Cl. .................................... 600/517
(58) Field of Classification Search ................. 600/517
See application file for complete search history.

(56) References Cited

U.S. PATENT DOCUMENTS

| | | | |
|---|---|---|---|
| 5,113,869 A * | 5/1992 | Nappholz et al. | 600/508 |
| 5,135,004 A | 8/1992 | Adams et al. | 128/696 |
| 5,199,428 A | 4/1993 | Obel et al. | 128/419 C |
| 5,203,326 A | 4/1993 | Collins | 128/419 PG |
| 5,313,953 A | 5/1994 | Yomtov et al. | 128/696 |
| 5,328,460 A | 7/1994 | Lord et al. | 604/67 |
| 6,016,443 A | 1/2000 | Ekwall et al. | 600/519 |
| 6,021,350 A | 2/2000 | Mathson | 607/17 |
| 6,108,577 A | 8/2000 | Benser | 600/517 |
| 6,112,116 A | 8/2000 | Fischell et al. | 600/517 |
| 6,115,628 A | 9/2000 | Stadler et al. | 600/517 |
| 6,128,526 A | 10/2000 | Stadler et al. | 600/517 |
| 6,233,486 B1 | 5/2001 | Ekwall et al. | 607/17 |
| 6,256,538 B1 | 7/2001 | Ekwall | 607/17 |
| 6,264,606 B1 | 7/2001 | Ekwall et al. | 600/300 |
| 6,266,554 B1 * | 7/2001 | Hsu et al. | 600/515 |
| 6,272,379 B1 | 8/2001 | Fischell et al. | 607/5 |

(Continued)

FOREIGN PATENT DOCUMENTS

EP   0 472 411 A1   2/1992

(Continued)

OTHER PUBLICATIONS

Breiman et al. "*Classification and Regression Trees—Introduction to Tree Classification,*" Wadsworth International Group, Belmont CA, (1984), pp. 18-43.

(Continued)

*Primary Examiner*—Carl H Layno
*Assistant Examiner*—Brian T Gedeon

(57) ABSTRACT

Pattern classification techniques are provided for use with an implantable medical device for detecting cardiac ischemia substantially in real-time. Values representative of morphological features of electrical cardiac signals are detected by the implantable medical device. Then, a determination is made as to whether the patient is subject to an on-going episode of cardiac ischemia by applying the values to a pattern classifier configured to identify patterns representative of cardiac ischemia. In one example, the determination is made substantially in real-time by the device itself based on the IEGM signals it detects. In other examples, the IEGM signals are relayed promptly to a bedside monitor or other external device, which analyzes the signals using the pattern classifier to detect ischemia. Therapy may be applied in response to cardiac ischemia. For example, if the implanted device is equipped with a drug pump, appropriate medications may be administered such as anti-thrombolytics.

20 Claims, 8 Drawing Sheets

U.S. PATENT DOCUMENTS

| | | | |
|---|---|---|---|
| 6,381,493 B1 * | 4/2002 | Stadler et al. | 607/9 |
| 6,501,983 B1 * | 12/2002 | Natarajan et al. | 600/517 |
| 6,519,493 B1 | 2/2003 | Florio et al. | 607/9 |
| 6,609,023 B1 | 8/2003 | Fischell et al. | 600/515 |
| 6,622,045 B2 | 9/2003 | Snell et al. | 607/30 |
| 6,678,669 B2 * | 1/2004 | Lapointe et al. | 706/15 |
| 6,823,213 B1 * | 11/2004 | Norris et al. | 607/9 |
| 7,218,960 B1 * | 5/2007 | Min et al. | 600/509 |
| 7,225,015 B1 * | 5/2007 | Min et al. | 600/517 |
| 7,265,676 B2 * | 9/2007 | Gordon et al. | 340/573.1 |
| 7,272,436 B2 * | 9/2007 | Gill et al. | 600/513 |
| 7,274,959 B1 * | 9/2007 | Wang et al. | 600/509 |
| 7,297,114 B2 * | 11/2007 | Gill et al. | 600/365 |
| 7,460,900 B1 * | 12/2008 | Gill et al. | 600/509 |
| 7,502,644 B2 * | 3/2009 | Gill et al. | 600/516 |
| 7,524,287 B2 * | 4/2009 | Bharmi | 600/365 |
| 2003/0045805 A1 | 3/2003 | Sheldon et al. | 600/513 |
| 2003/0158492 A1 | 8/2003 | Sheldon et al. | 600/508 |
| 2006/0206158 A1 * | 9/2006 | Wu et al. | 607/17 |
| 2007/0129639 A1 * | 6/2007 | Zhang et al. | 600/509 |
| 2007/0156056 A1 * | 7/2007 | Min et al. | 600/509 |

FOREIGN PATENT DOCUMENTS

| | | |
|---|---|---|
| EP | 0 867 146 B1 | 9/1998 |
| EP | 1 400 259 A1 | 3/2004 |
| WO | WO 00/ 64534 | 11/2000 |
| WO | WO 03/ 020367 A1 | 3/2003 |
| WO | WO 2004/047917 A1 | 6/2004 |

OTHER PUBLICATIONS

T. Hastie et al., "*The Elements of Statistical Learning*," Springer (2001), pp. 79-108—Linear Method for Classification and pp. 371-402—Support Vector Machines and Flexible Discriminants.

\* cited by examiner

SYSTEM AND METHOD FOR DETECTING CARDIAC ISCHEMIA IN REAL-TIME USING A PATTERN CLASSIFIER IMPLEMENTED WITHIN AN IMPLANTED MEDICAL DEVICE

FIELD OF THE INVENTION

The invention generally relates to implantable medical devices such as pacemakers and implantable cardioverter/defibrillators (ICDs) and, in particular, to techniques for detecting cardiac ischemia using such devices.

BACKGROUND OF THE INVENTION

Cardiac ischemia is a condition whereby heart tissue does not receive adequate amounts of oxygen and is usually caused by a blockage of an artery leading to heart tissue. If sufficiently severe, cardiac ischemia results in an acute myocardial infarction (AMI), also referred to as a heart attack. With AMI, a substantial portion of heart muscle ceases to function because it no longer receives oxygen, usually due to significant blockage of the coronary artery. Generally, AMI occurs when plaque (such as fat, cholesterol, and calcium) builds up and then ruptures in the coronary artery, allowing a blood clot or thrombus to form. Eventually, the blood clot completely blocks the coronary artery and so heart tissue beyond the blockage no longer receives oxygen and the tissue dies. In many cases, an AMI proves fatal because too much tissue is damaged to allow continued functioning of the heart muscle. Indeed, AMI is a leading cause of death here in the United States and worldwide. In other cases, although the AMI itself is not fatal, it strikes while the victim is engaged in potentially dangerous activities, such as driving vehicles or flying airplanes, and the severe pain and possible loss of consciousness associated with AMI results in fatal accidents. Even if the victim survives the AMI, quality of life may thereafter be severely restricted.

Often AMI is preceded by episodes of cardiac ischemia that are not sufficiently serious to cause actual permanent injury to the heart tissue. Nevertheless, these episodes are often precursors to AMI. Episodes of cardiac ischemia may also trigger certain types of arrhythmias that may prove fatal, particularly ventricular fibrillation (VF) wherein the ventricles of the heart beat chaotically, resulting in little or no net flow of blood from the heart to the brain and other organs. Indeed, serious episodes of cardiac ischemia (referred to herein as acute myocardial ischemia) typically result in either a subsequent AMI or VF, often within one to twenty-four four hours, sometimes within only a half an hour or less. Accordingly, it would be highly desirable to provide a technique for reliably detecting cardiac ischemia in real-time so that the victim may be warned and medical attention sought. If properly warned, surgical procedures may be implemented to locate and remove the growing arterial blockage or anti-thrombolytic medications may be administered. At the very least, such warnings would allow the victim to cease activities that might result in a fatal accident. Moreover, in many cases, AMI or VF is triggered by strenuous physical activities and so ischemia warnings would allow the victim to cease such activities, possibly preventing AMI or VF from occurring.

Many patients at risk of cardiac ischemia have pacemakers, ICDs or other medical devices implanted therein, or are candidates for such devices. Accordingly, techniques have been developed for detecting cardiac ischemia using implanted medical devices. In particular, techniques have been developed for analyzing intracardiac electrogram (IEGM) signals sensed by such devices in an effort to detect cardiac ischemia. See, for example, U.S. Pat. No. 6,108,577 to Benser, entitled "Method and Apparatus for Detecting Changes in Electrocardiogram Signals." See, also, U.S. Pat. Nos. 5,113,869 to Nappholz; 5,135,004 to Adams et al.; 5,199,428 to Obel et al.; 5,203,326 to Collins; 5,313,953 to Yomtov et al; 6,501,983 to Natarajan, et al.; 6,016,443, 6,233,486, 6,256,538, and 6,264,606 to Ekwall; 6,021,350 to Mathson; 6,112,116 and 6,272,379 to Fischell et al; 6,128,526, 6,115,628 and 6,381,493 to Stadler et al; and. Many IEGM-based ischemia detection techniques seek to detect ischemia by identifying changes in the elevation of the ST segment of the IEGM that occur during cardiac ischemia. The ST segment represents the portion of the cardiac signal between ventricular depolarization (also referred to as an R-wave or QRS complex) and ventricular repolarization (also referred to as a T-wave). The QRS complex usually follows an atrial depolarization (also referred to as a P-wave.) Strictly speaking, P-waves, R-waves and T-waves are features of a surface electrocardiogram (EKG). For convenience and generality, the terms P-wave, T-wave and T-wave are used herein to refer to the corresponding internal signal component as well.

A significant concern with any cardiac ischemia detection technique that relies on changes in the ST segments is that systemic influences within the patient can alter the ST segment. For example, hypoglycemia (low blood sugar levels) and hyperglycemia (high blood sugar levels) can both affect ST segment elevation. In addition, electrolyte imbalance, such as hypokalemia (low potassium levels) or hyperkalemia (high potassium levels) can affect the ST segment. Certain anti-arrhythmic drugs can also affect the ST-segment.

Accordingly, it would be desirable to provide alternative techniques for detecting cardiac ischemia in real-time, which do not rely exclusively on ST segment elevation, and it is to that end that the invention is directed.

SUMMARY OF THE INVENTION

In accordance with the invention, pattern classification techniques are provided for use with an implantable medical device for detecting cardiac ischemia in a patient in which the device is implanted. A plurality of values representative of different morphological features of IEGM signals or other electrical cardiac signals are detected by the implantable medical device. Then a determination is made as to whether the patient is subject to an on-going episode of cardiac ischemia by applying the values to a pattern classifier configured to identify patterns representative of cardiac ischemia. In one example, the determination is made substantially in real-time by the device itself based on the IEGM signals it detects. In other examples, the IEGM signals are relayed promptly to a bedside monitor or other external device, which analyzes the signals using the pattern classifier to detect ischemia. In either case, by using a pattern classifier to detect ischemia based on IEGM signals or other cardiac electrical signals, cardiac ischemia can be detected substantially in real-time while exploiting a variety of morphological features of the IEGM, thereby avoiding the disadvantages of techniques that rely primarily or exclusively on ST segment deviation.

Preferably, the morphological features detected within the IEGM include one or more of atrial depolarization events (P-waves), ventricular depolarization events (QRS-complexes), and ventricular repolarization events (T-waves). The specific values representative of the morphological features that are applied to the pattern classifier can include parameters pertaining to one or more of: event duration (e.g. P-wave width, QRS-complex width and T-wave width); event slope (e.g. maximum P-wave slope, maximum QRS-complex slope and maximum T-wave slope); event amplitude (e.g. peak P-wave amplitude, peak QRS-complex amplitude and peak T-wave amplitude); and event intervals (e.g. AV intervals and ST intervals.)

During an initial setup or calibration phase, the pattern classifier is preferably trained to recognize cardiac ischemia based on morphological features of electrical cardiac signals associated with cardiac ischemia. For example, sets of values associated with known episodes of cardiac ischemia are applied to the pattern classifier so as to train the pattern classifier to recognize cardiac ischemia.

In one example, the pattern classifier is a linear discriminant-based pattern classifier. Once the linear discriminant-based classifier has been trained, ischemia detection is performed by applying the values to the classifier to generate a classification metric and then comparing the classification metric to a threshold representative of cardiac ischemia. If the classification metric exceeds the threshold, a signal indicating an ischemic condition is generated. In another example, the pattern classifier is a classification tree-based pattern classifier. Once the tree-based pattern classifier has been trained, ischemia detection is performed by applying the values to the classification tree to classify the values as either being ischemic or non-ischemic. A signal indicative of the detection of cardiac ischemia is generated if the classification tree classifies the values as ischemic.

In one particular implementation, morphological features of only the latest heartbeat of the patient are applied to the pattern classifier so as to achieve substantially real-time ischemia detection. In other implementations, morphological features of a plurality of recent heartbeats are applied to the pattern classifier, preferably averaged before being applied to the pattern classifier. For example, morphological parameters corresponding to all heartbeats detected over the preceding thirty seconds may be averaged and then applied to the pattern classifier so as to permit periodic analysis of ischemia.

Upon detecting of the onset of an episode of cardiac ischemia, appropriate warning signals are generated, which can include both "tickle warning" signals applied to subcutaneous tissue and short range telemetry warning signals transmitted to a device external to the patient. In one example, once the tickle warning is felt, the patient positions an external warning device above his or her chest. The handheld device receives the short-range telemetry signals and provides audible or visual verification of the warning signal. The handheld warning device thereby provides confirmation of the warning to the patient, who may be otherwise uncertain as to the reason for the internally generated warning signal.

Therapy may also be applied or modified by the implanted system in response to cardiac ischemia, depending upon the capabilities of the implanted system. For example, if the implanted system is equipped with a drug pump, appropriate medications may be administered, particularly anti-thrombolytic drugs. If overdrive pacing is being applied by the system, overdrive pacing is preferably deactivated to prevent the increased heart rate associated with overdrive pacing from exacerbating the ischemia. If the system has defibrillation capabilities, the system may immediately begin charging defibrillation capacitors upon detection of cardiac ischemia to permit prompt delivery of a defibrillation shock if the ischemia triggers VF. Additionally, or in the alternative, diagnostic information pertaining to ischemia may be stored for subsequent review by a physician.

Hence, improved techniques are provided for detecting cardiac ischemia. The techniques are preferably performed by the implanted medical device itself to provide prompt warnings of ischemia and to delivery appropriate therapy. Alternatively, the techniques may be performed by external devices, such as bedside monitors or the like, based on IEGM signals detected by the implanted device and transmitted to the external device. System and method implementations of the techniques are described herein.

BRIEF DESCRIPTION OF THE DRAWINGS

The above and further features, advantages and benefits of the present invention will be apparent upon consideration of the present description taken in conjunction with the accompanying drawings, in which.

DETAILED DESCRIPTION OF THE PREFERRED EMBODIMENTS

The following description includes the best mode presently contemplated for practicing the invention. This description is not to be taken in a limiting sense but is made merely to describe general principles of the invention. The scope of the invention should be ascertained with reference to the issued claims. In the description of the invention that follows, like numerals or reference designators are used to refer to like parts or elements throughout.

Overview of Implantable System

Figure 1:
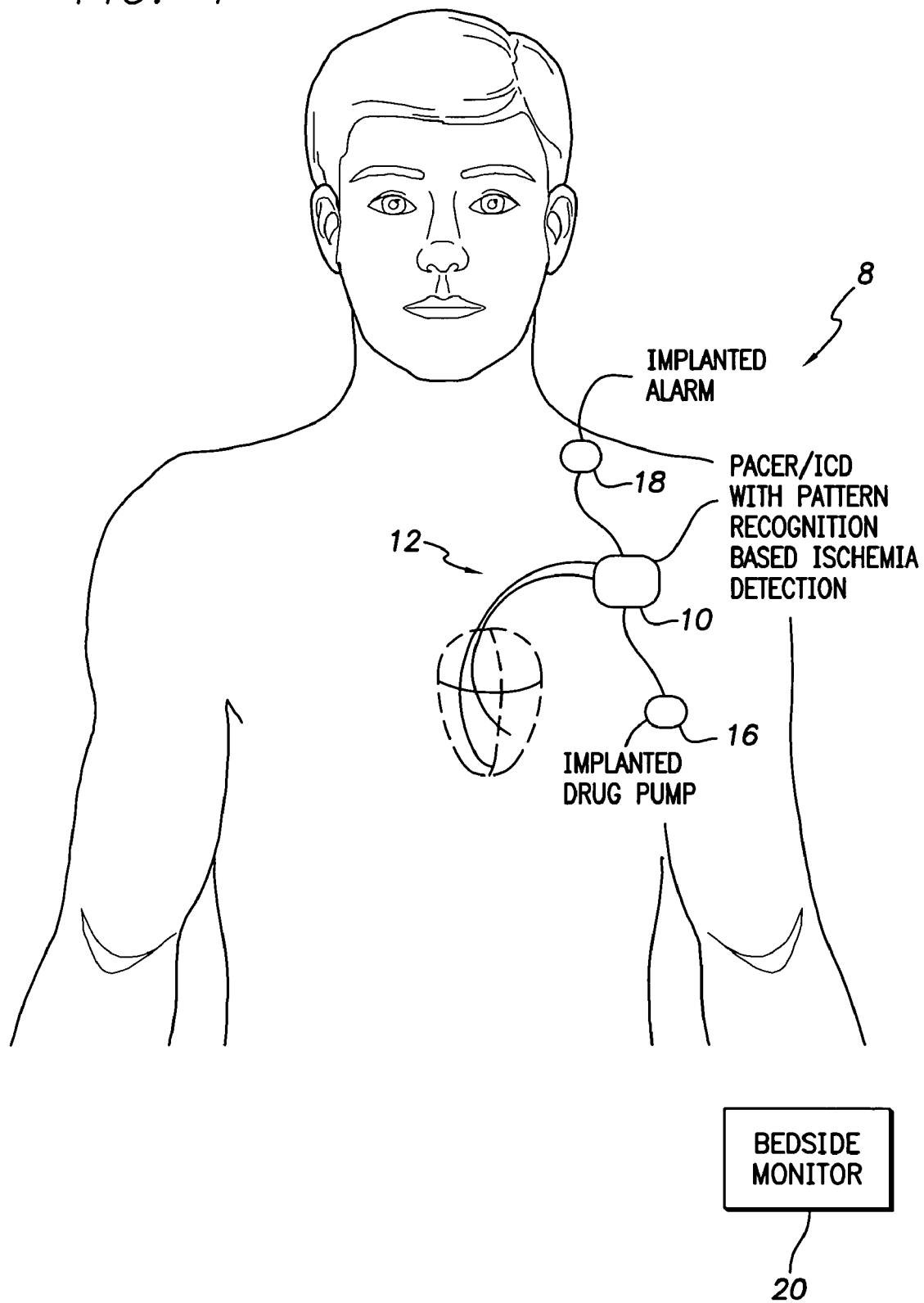
FIG. 1 illustrates pertinent components of an implantable medical system having a pacemaker or ICD capable of evaluating cardiac ischemia based on pattern recognition and delivering therapy or warning signals in response thereto.
Figure 8:
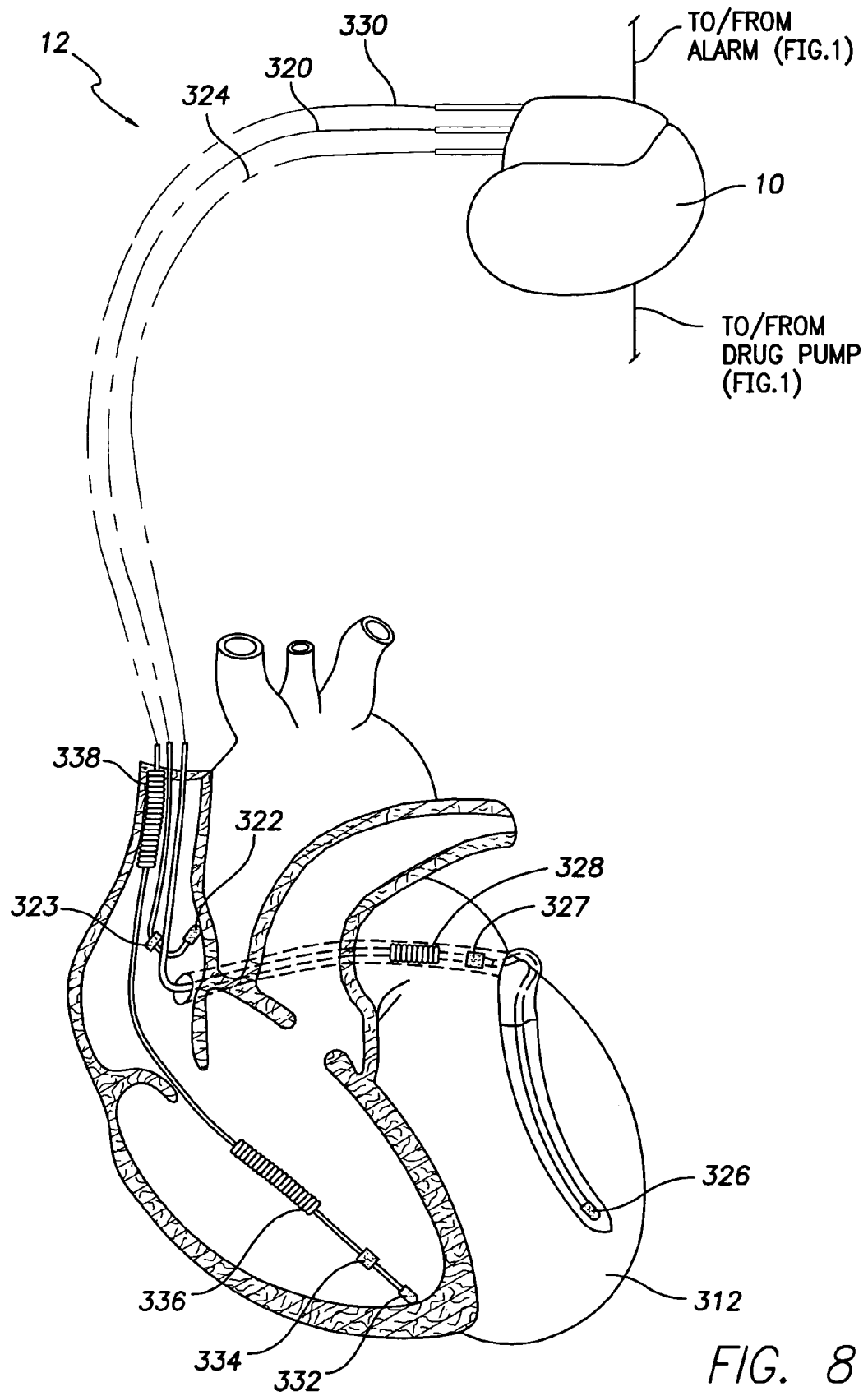
FIG. 8 is a simplified, partly cutaway view, illustrating the pacer/ICD of FIG. 1 along with a full set of leads implanted into the heart of the patient.

FIG. 1 illustrates an implantable medical system 8 capable of detecting cardiac ischemia substantially in real-time. System 8 includes a pacer/ICD 10 or other cardiac stimulation device equipped with internal components for detecting cardiac ischemia via pattern recognition using IEGM signals and for controlling the delivery of therapy and warnings in response thereto. To detect cardiac ischemia, pacer/ICD 10 senses IEGM signals or electrical cardiac signals, identifies selected morphological features therein and then applies values representative of those features to a pattern recognition unit trained to recognize features indicative of cardiac ischemia. More specifically, the pacer/ICD receives electrical cardiac signals from a set of cardiac pacing/sensing leads 12 implanted within the heart of the patient from which the IEGM is derived. In FIG. 1, only two pacing leads are shown. A full set of pacing leads is shown in FIG. 8. As will be explained more fully below, pattern recognition is preferably performed using either linear discriminator-based pattern recognition techniques or tree-based classification techniques.

If cardiac ischemia is detected, appropriate therapy is automatically delivered by the implantable system under the control of the pacer/ICD. For example, anti-thrombolytics or other appropriate medications may be automatically delivered via an implanted drug pump 16. Warning signals are also generated using either an internal warning device 18 or an external bedside monitor 20 so as to notify the patient of the onset of an episode of cardiac ischemia. Internal warning device 18 may be a vibrating device or a "tickle" voltage device that, in either case, provides perceptible stimulation to the patient to alert the patient. The bedside monitor 20 provides audible or visual alarm signals to alert the patient, as well as textual or graphic displays. In addition, once cardiac ischemia has been detected, diagnostic information is generated within the pacer/ICD for transmission to the bedside monitor or for subsequent transmission to an external programmer (not shown in FIG. 1) for review by a physician or other medial professional. The physician may then prescribe any other appropriate therapies to prevent additional episodes of cardiac ischemia. The physician may also adjust the operation of the pacer/ICD to activate, deactivate or otherwise control any therapies that are automatically applied. The bedside monitor may be directly networked with a centralized computing system for immediately notifying a nurse or physician of the episode of cardiac ischemia.

Hence, FIG. 1 provides an overview of an implantable system for detecting cardiac ischemia and delivering appropriate therapy. Systems provided in accordance with the invention need not include all the components shown in FIG. 1. In many cases, for example, the system will include only the pacer/ICD and its leads. Drug pumps and warning devices are not necessarily implanted. In addition, although internal signal transmission lines are illustrated in FIG. 1 for interconnecting the various implanted components, wireless signal transmission may alternatively be employed. In addition, the particular locations of the implanted components shown in FIG. 1 are merely illustrative and may not necessarily correspond to actual implant locations.

Overview of the Pattern Recognition-Based Ischemia Detection Technique

Figure 2:
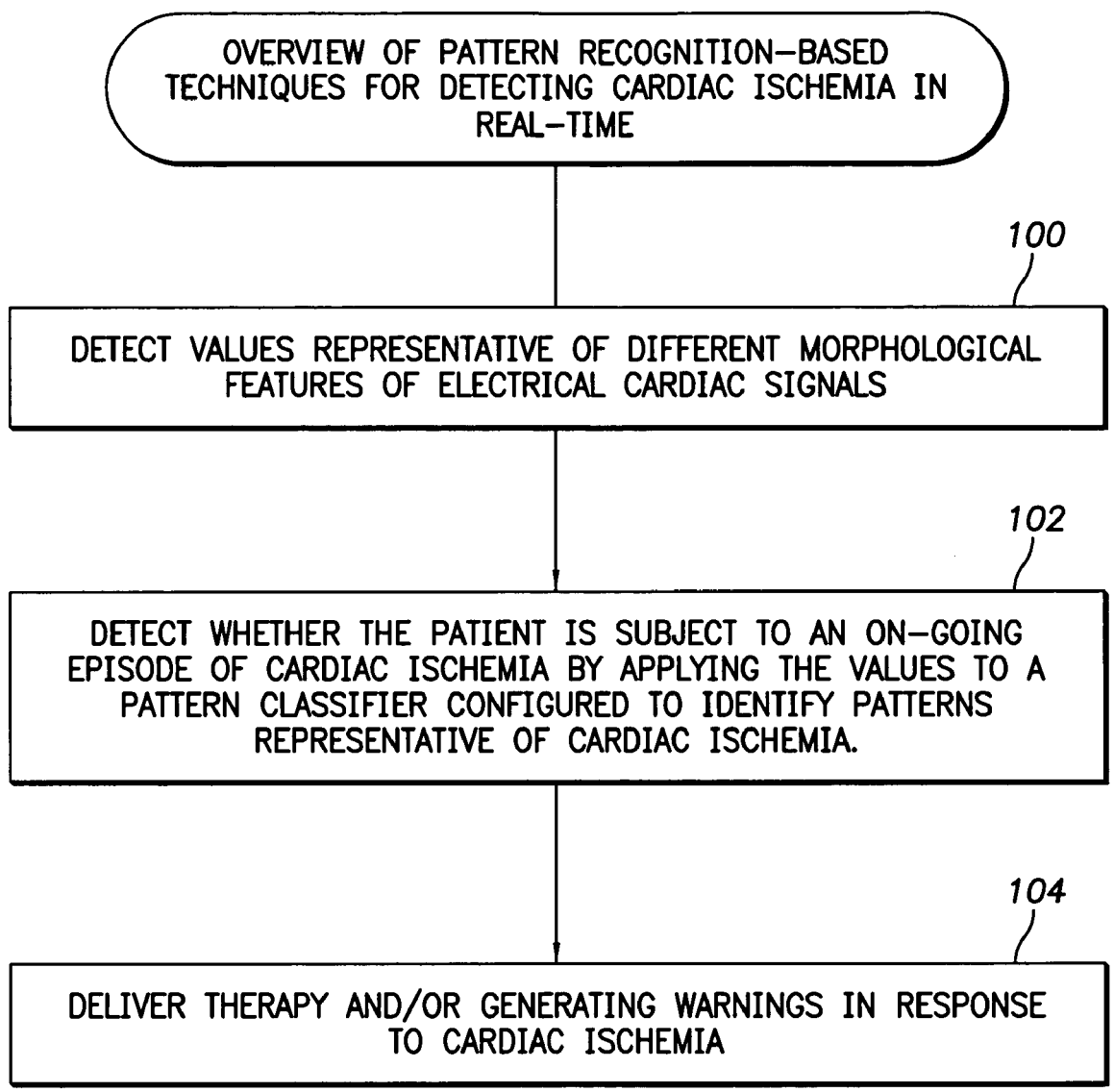
FIG. 2 is a flow diagram providing a high-level overview of the technique for detecting cardiac ischemia performed by the system of FIG. 1.
Figure 3:
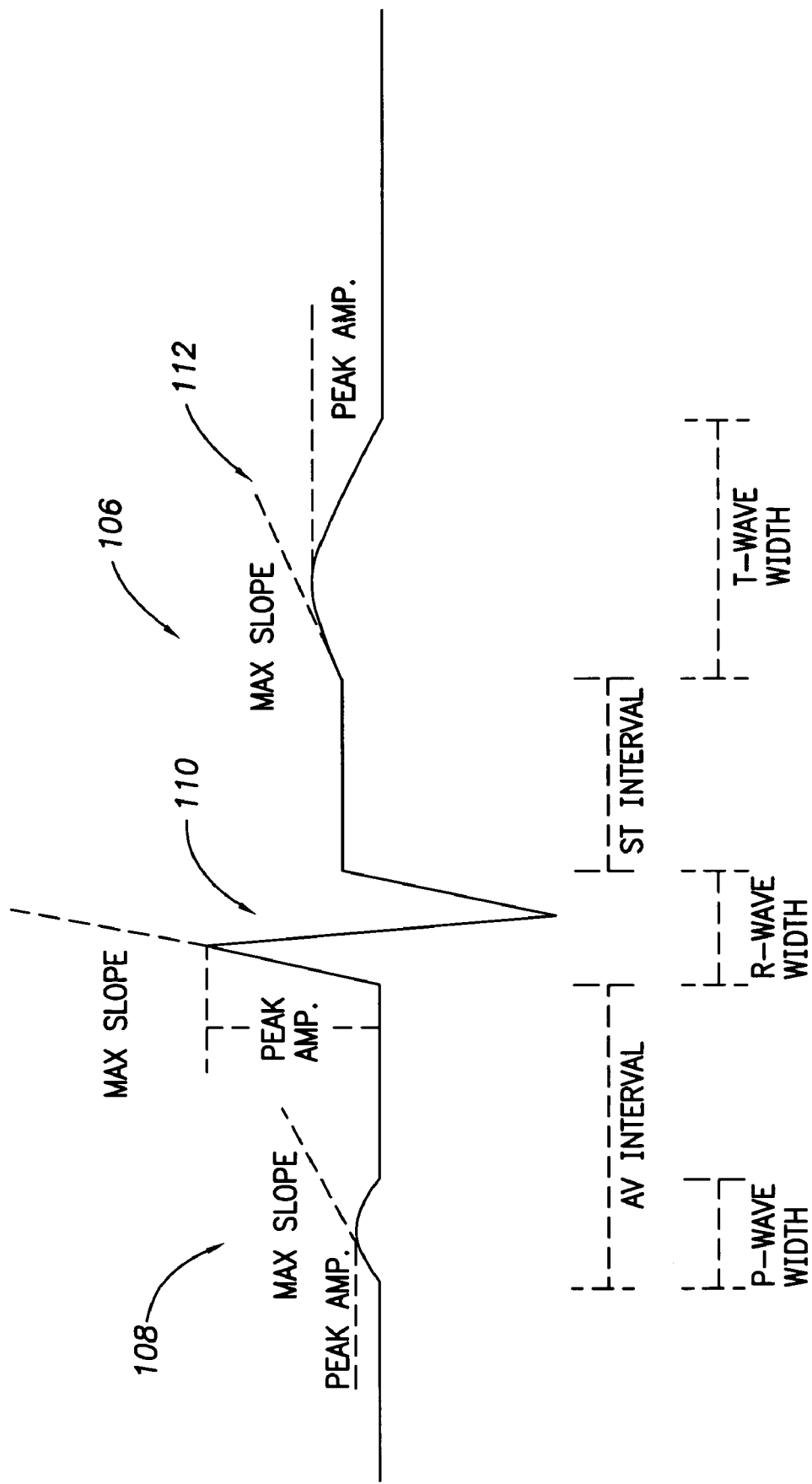
FIG. 3 sets forth a stylized diagram of the IEGM of a single patient heartbeat, particularly illustrating certain morphological parameters of the heartbeat exploited by the cardiac ischemia detection technique of FIG. 2.

FIGS. 2-3 summarize the pattern recognition-based cardiac ischemia detection technique of the invention that may be performed using the system of FIG. 1. Briefly, at step 100, the pacer/ICD detects a plurality of values representative of different morphological features of an IEGM or other electrical cardiac signal. At step 102, the pacer/ICD detects whether the patient is subject to an on-going episode of cardiac ischemia by applying the values detected at step 100 to a pattern classifier configured to identify or recognize patterns representative of cardiac ischemia. At step 104, the pacer/ICD delivers any appropriate therapy and/or generates any appropriate warnings in response to the detection of cardiac ischemia. In general, any combination of different morphological values or parameters can be detected at step 100, so long as the values can be reliably correlated with cardiac ischemia to permit detection of cardiac ischemia via pattern recognition techniques. Values corresponding to at least two different morphological features are used so as to permit pattern recognition.

FIG. 3 illustrates the primary morphological features of an intrinsic (i.e. un-paced) heartbeat 106, including the P-wave 108, QRS-complex 110 and T-wave 112 (all shown in stylized form.) Each of these primary features is characterized by various particular morphological features, such as width, peak amplitude, maximum slope, etc., as shown in FIG. 3. Numerical values corresponding to these particular features are detected at step 100 of FIG. 2. Additionally, selected intervals between individual features are also preferably detected, such as the atrioventricular (AV) interval between the P-wave and the QRS-complex and the ST segment interval between the end of the QRS-complex and the T-wave.

The precise parameters that are detected may be defined in any of a variety of various ways, depending upon the particular implementation, so long as the pacer/ICD is consistent. For example, "P-wave width" may be defined as the interval between the very beginning and very end of the P-wave, as shown in FIG. 3. Alternatively, the width may be defined as a "full width/half maximum." In other examples, the width is defined as the interval between when the absolute magnitude of an atrial channel signal first exceeds an atrial channel sensing threshold (not shown) and when it subsequently falls below that sensing threshold. So long as the pacer/ICD is consistent from one P-wave to another, any suitable definition of "P-wave width" may be employed. As another example, "maximum slope" may be defined as the maximum positive slope or the maximum negative slope. The AV interval may be defined, as shown, between the beginning of the P-wave and the beginning of the QRS-complex. However, in other implementations, the AV interval is defined as the interval between when the P-wave is first detected based on the atrial channel sensing threshold and when the QRS-complex is detected based on a ventricular channel sensing threshold (not shown). In the example of FIG. 3, a sensed (i.e. intrinsic) P-wave is shown along with a sensed (i.e. intrinsic) the QRS complex. Parameters may also be defined with respect to paced atrial and ventricular events. Furthermore, the particular parameters illustrated in FIG. 3 are merely exemplary. Other parameters that characterize aspects of the morphological features of the IEGMs may additionally or alternatively be used. For example, the integral or sum of the area associated with a morphological feature may be detected, including a paced depolarization integral (PDI). Energy or frequency values associated with morphological features may be detected.

Parameters associated with individual heartbeats are generally preferred as such parameters permit ischemia to be detected substantially in real-time. However, depending upon implementation, parameters associated with multiple heartbeats may additionally or alternatively be used. For example, intervals between features of consecutive heartbeats may be detected, such as R-R intervals and P-P intervals. In addition, R-R variability and P-P variability may be detected and exploited. As noted, any combination of morphological parameters of electrical cardiac signals that can be reliably correlated with cardiac ischemia can be exploited for the purposes of detection of ischemia via pattern recognition. Otherwise routine experimentation may be employed to identify particular combinations of morphological parameters that are sufficiently correlated with ischemia to permit reliable detection of ischemia via pattern recognition techniques.

With reference to the remaining figures, the techniques invention will now be described in greater detail.

Exemplary Implementations of the Pattern Recognition-Based Techniques

Figure 4:
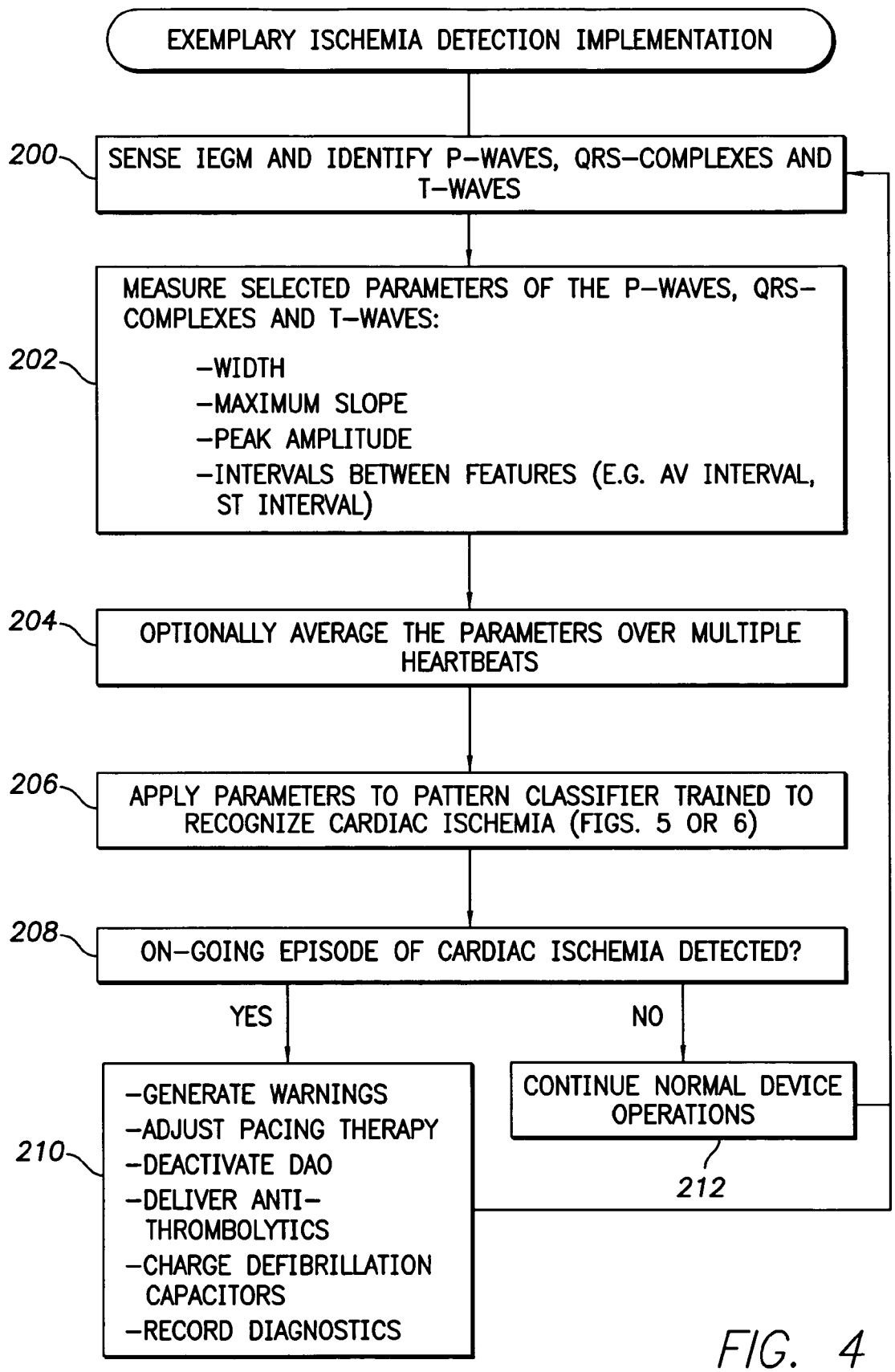
FIG. 4 is a flow diagram illustrating an exemplary technique for detecting cardiac ischemia and delivering therapy in response thereto using a pattern recognition system in accordance with the general technique of FIG. 2.

FIG. 4 illustrates an exemplary ischemia detection implementation. Beginning at step 200, the pacer/ICD senses the IEGM of the patient identifies P-waves, QRS-complexes and T-waves therein corresponding to individual heartbeats of the patient. At step 202, the pacer/ICD measures selected parameters of the P-waves, QRS-complexes and T-waves, including the width, maximum slope, and peak amplitude of each. Additionally, the pacer/ICD detects of the AV interval and the ST interval. At step 204, optionally, the pacer/ICD averages the detected parameters over multiple heartbeats. For example, parameters may be averaged over all heartbeats detected over a predetermined interval, such as the last 30 seconds. Either each parameter is individually averaged (i.e. all P-wave width values are averaged together, all P-wave peak amplitude values are averaged together, etc.) or an ensemble average is taken (e.g. all parameters associated with the P-wave are averaged together, all parameters associated with the QRS-complex are averaged together, etc.) In other implementations, parameters are not averaged. Averaging may improve the reliability of the cardiac ischemia detection. However, ischemia detection substantially in real-time is more readily achieved when parameters are not averaged over multiple heartbeats.

At step 206, the parameters (averaged or otherwise) are then applied to a pattern classifier within the pacer/ICD, which has been trained to recognize cardiac ischemia. Exemplary pattern classifiers will be described below with reference to FIGS. 5 and 6. Training will be described below with reference to FIG. 7. The output of the pattern recognizer is either "ischemic" or "non-ischemic," i.e., either the detected parameters are correlated with an ongoing episode of ischemia or they are not. If the detected parameters have been averaged over multiple heartbeats, then a single "ischemic" output from the pattern recognizer is deemed to indicate of an ongoing episode of ischemia. If the detected parameters correspond only to a single heartbeat (i.e. the parameters have not been averaged over multiple heartbeats) then, preferably, a single "ischemic" output from the pattern recognizer is not yet deemed to indicate an ongoing episode of ischemia. Rather, some predetermined number of ischemic indications is required. For example, some predetermined number of consecutive heartbeats (e.g. three) must all be indicative of ischemia, or some predetermined number of heartbeats out of latest sequence of heartbeats (e.g. three out of the last ten heartbeats) are indicative of ischemia, or some predetermined number of heartbeats over a set period of time (e.g. three heartbeats within of the last twenty seconds) are indicative of ischemia. All of these parameters are preferably programmable and adjustable by the physician.

If, at step 208, an on-going episode of cardiac ischemia is indicated, then step 210 is performed wherein the pacer/ICD: (1) generates warnings; (2) adjusts pacing therapy; (3) deactivates dynamic atrial overdrive (DAO) pacing (if it is currently being applied); (4) delivers anti-thrombolytics or other appropriate medications via a drug pump; (5) charges defibrillation capacitors (if the pacer/ICD is equipped to deliver defibrillation shocks); and/or (6) records the appropriate diagnostics.

Warnings may be delivered, if so equipped, by an implanted warning device such as a "tickle" voltage warning device. "Tickle" warning device are discussed in U.S. Pat. No. 5,328,460 to Lord, et al., entitled "Implantable Medication Infusion Pump Including Self-Contained Acoustic Fault Detection Apparatus." Alternatively, or additionally, warnings may be relayed to an external warning device, such as a bedside monitor. If the bedside monitor is within a hospital or clinic, the warnings are preferably also relayed to the nearest nurse's station, physician's office, or the like. A system incorporating bedside monitoring units connected to a centralized external programmer system is described in U.S. Pat. No. 6,622,045 to Snell et al., "System and Method for Remote Programming of Implantable Cardiac Stimulation Devices."

Adjustments to pacing therapy in response to cardiac ischemia may involve, for example, reduction of a base pacing rate so as to prevent a relatively high programmed base rate from exacerbating the ischemia. As noted, DAO is preferably deactivated, again to prevent exacerbation of the ischemia. DAO is described in U.S. Pat. No. 6,519,493 to Florio et al., entitled "Methods and Apparatus for Overdrive Pacing Heart Tissue Using an Implantable Cardiac Stimulation Device." Anti-thrombolytics or other medications are preferably delivered using an implanted drug pump, if one is provided. The aforementioned patent to Lord et al. also discusses implantable drug pumps. Routine experimentation may be employed to identify medications for treatment of cardiac ischemia that are safe and effective for use in connection with an implantable drug pump. Diagnostic information stored at step 210 may include the date/time of the detection of an episode of ischemia, the duration of the episode, and the particular morphological parameters that triggered the detection.

In some implementations, prior to delivering therapy or generating warnings, the pacer/ICD corroborates the detection of ischemia using other ischemia detection techniques, such as the ST interval-based techniques discussed above or various non-ST interval based techniques. See, for example, U.S. patent application Ser. No. 10/603,429, entitled "System and Method for Detecting Cardiac Ischemia Using an Implantable Medical Device", of Wang et al., filed Jun. 24, 2003. Rather than examine the ST segment, the technique of Wang et al. instead examines post-T-wave segments, i.e. that portion of the cardiac signal immediately following the T-wave. In one example, the onset of cardiac ischemia is identified by detecting a sharp falling edge within post-T-wave signals. Another technique for detecting cardiac ischemia based on T-waves is set forth in U.S. patent application Ser. No. 10/603,398, entitled "System And Method For Detecting Cardiac Ischemia Based On T-Waves Using An Implantable Medical Device", of Min et al., filed Jun. 24, 2003. With the technique of Min et al., cardiac ischemia is detected based either on the total energy of the T-wave or on the maximum slope of the T-wave. In one example, warnings and therapy are only delivered if the corroboratory techniques also indicate a high likelihood of cardiac ischemia.

If an episode of ischemia is not indicated at step 208, then step 212 is performed wherein the pacer/ICD continues its normal operations.

Figure 5:
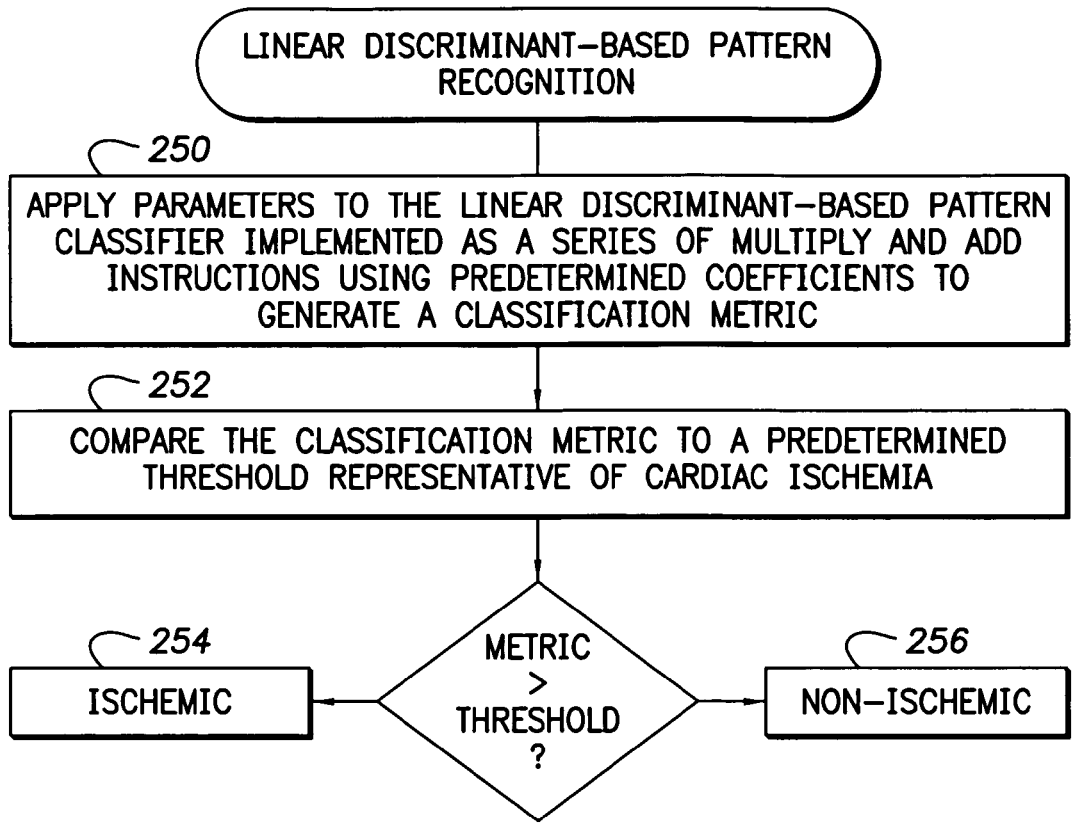
FIG. 5 is a flow diagram illustrating a particular technique for detecting cardiac ischemia using a linear discriminator for use with the exemplary technique of FIG. 4.
Figure 6:
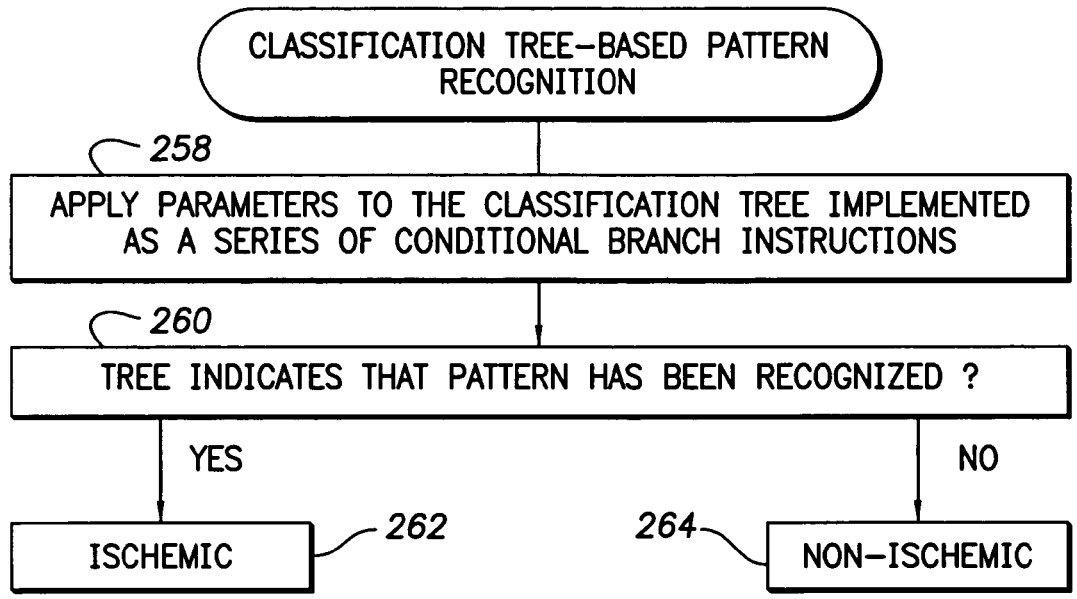
FIG. 6 is a flow diagram illustrating a particular technique for detecting cardiac ischemia using a tree classification system for use with the exemplary technique of FIG. 4.

Turning now to FIGS. 5 and 6, exemplary pattern classifications techniques for use at step 206 of FIG. 4 will now be described. In particular, FIG. 5 summarizes steps performed using a linear discriminant-based pattern classifier that has been trained (FIG. 7) to classify heartbeat morphological patterns as being either ischemic or non-ischemic. At step 250, the parameters detected at step 202 of FIG. 4 (averaged or otherwise) are applied to the linear discriminant-based pattern classifier to generate a classification metric. At step 252, the classification metric is then compared to a predetermined threshold representative of cardiac ischemia. If the metric exceeds the threshold then, at step 254, an "ischemic" indication is output by the classifier. Otherwise, a "non-ischemic" indication is output at step 256.

Figure 7:
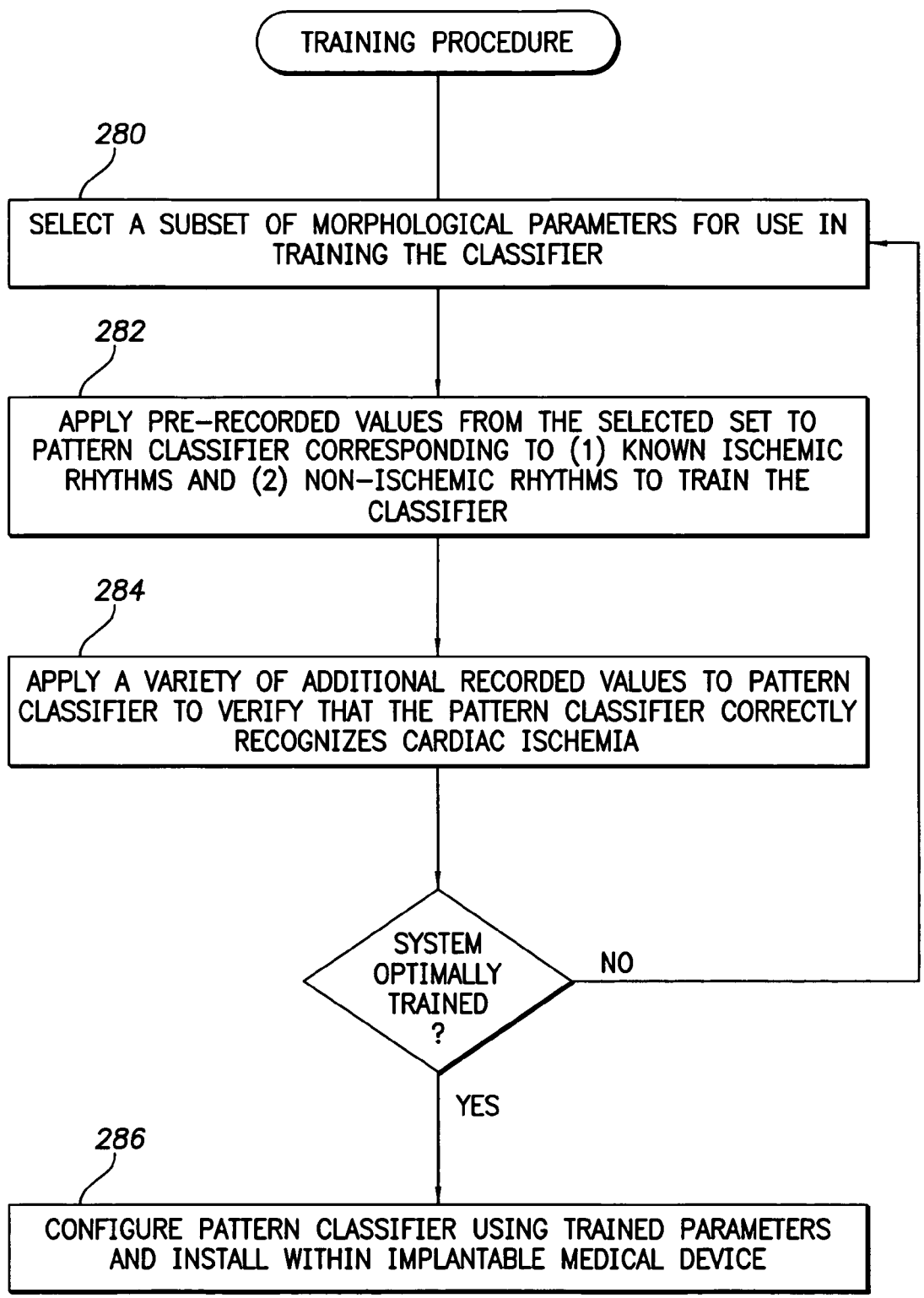
FIG. 7 is a flow diagram illustrating a training procedure for training the pattern recognition system used by the exemplary technique of FIG. 2 to recognize cardiac ischemia.

The linear discriminant-based classifier may be implemented in the pacer/ICD as a series of multiply and add instructions in microcontroller code using predetermined coefficients, with the sum of the terms being the metric that is compared to the threshold. Alternatively, the classifier maybe configured as an application specific integrated circuit (ASIC) or other hardware device. The coefficients for use with the classifier are determined as part of the training process (FIG. 7). The threshold to be used is also determined or otherwise specified during the training process, but is adjustable by the physician.

Turning now to FIG. 6, steps performed using a classification tree-based pattern classifier will now be summarized. As with the linear discriminant-based classifier, the classification tree-based classifier is trained (FIG. 7) to classify heartbeat morphological patterns as being either ischemic or non-ischemic. At step 258, the parameters detected at step 202 of FIG. 4 (averaged or otherwise) are applied to the linear classification tree. At step 260, the classification tree outputs a signal indicating whether the morphological patterns have been recognized. If recognized then, at step 262, an "ischemic" indication is output by the classifier. Otherwise, a "non-ischemic" indication is output at step 264.

A classification tree may be implemented in the pacer/ICD as a series of conditional branch instructions in microcontroller code. A hardware implementation is also suitable. The particular values against which the morphological parameters are to be compared at each conditional branch step, the number of comparisons to be made, and the order in which the comparisons are made are all determined as part of the training process.

Other appropriate pattern classification techniques or devices may alternatively be used, such as neural networks.

Turning now to FIG. 7, the training process for configuring the classifier will now be described. The process of configuring the classifier is preferably performed during the research and development (R&D) phase of the design of the pacer/ICD using training and testing sets of expert-classified IEGM data. More specifically, at step 280, a particular combination of morphological parameters is selected, such as a particular subset of the various parameters listed within step 202 of FIG. 4. For example, the selected subset may specify P-wave and T-wave widths, P-wave and T-wave maximum slopes, QRS-complex peak amplitude, and ST interval lengths. At step 282, pre-recorded examples of values from the subset of morphological parameters are then applied to the pattern classifier, e.g. individual width values, maximum slope values, peak amplitude values, etc. corresponding to individual heartbeats are applied to the classifier for training the classifier to recognize cardiac ischemia.

Preferably, at least two sets of values are applied: (1) "ischemic" sets corresponding to known episodes of cardiac ischemia and (2) "non-ischemic" sets corresponding to known non-ischemic cardiac rhythms, such as normal sinus rhythms. The sets of values corresponding to known episodes of ischemia are applied while specifying the output of the pattern classifier as "ischemic." The sets of parameters corresponding to non-ischemic cardiac rhythms are applied while specifying the output of the pattern classifier as "non-ischemic." The pattern classifier, in accordance with otherwise conventional techniques, determines the appropriate internal coefficients, threshold values, and the like required to reliably correlate ischemic input parameters to the ischemic output state and to correlate non-ischemic input parameters to the non-ischemic output state. Preferably, numerous examples of each of set of data are applied, subject to appropriate degrees of statistical variance, so as to achieve a robust pattern classifier.

There are many suitable algorithms described in the literature for training (i.e. optimally configuring) pattern classifiers. Many such algorithms are available in commercial statistical exploration software packages such as SPLUS, SAS and R (which are trademarks of their respective owners). See also techniques generally described in: Breiman et al. "Classification and Regression Trees", pages 18-43, Wadsworth International Group, Belmont Calif., (1984); and Hastie et al., "The Elements of Statistical Learning", pages 79-108 and 371-402, Springer, (2001).

Then, at step 284, additional prerecorded values of the selected parameters are applied to the pattern recognition system to verify that the system correctly recognizes cardiac ischemia. If the system has been properly trained, i.e. the classifier correctly classifies ischemic input parameters with ischemia and vice versa, then the trained pattern recognition parameters (i.e. particular coefficients, internal thresholds, and the like) are then used at step 286 to configure a pattern recognition unit (either as hardware or software) for installation within the pacer/ICD. Otherwise, the training procedure is repeated using additional prerecorded values. If necessary, a different set of parameters are selected at step 280. For example, if the exemplary combination of parameters listed above is insufficient to allow the classifier to reliably detect ischemia, then additional or alternative parameters are used, such as AV intervals or QRS-complex maximum slope. Ultimately, an optimal set of parameters are selected that permits the pattern classifier to reliably detect cardiac ischemia and the various resulting pattern recognition coefficients, thresholds, etc. are then used at step 286.

For the sake of completeness, a description of an exemplary pacer/ICD will now be provided. As many patients who suffer from cardiac ischemia are also candidates for pacer/ICDs, it is advantageous to configure a pacer/ICD to serve as the controller of the cardiac ischemia detection system. The techniques of the invention, however, may be performed using any suitable implantable components.

Exemplary Pacer/ICD

FIG. 8 provides a simplified block diagram of the pacer/ICD of FIG. 1, which is a dual-chamber stimulation device capable of treating both fast and slow arrhythmias with stimulation therapy, including cardioversion, defibrillation, and pacing stimulation, as well as capable of detecting cardiac ischemia and controlling the delivery of therapy and warnings in response thereto. To provide atrial chamber pacing stimulation and sensing, pacer/ICD 10 is shown in electrical communication with a heart 312 by way of a left atrial lead 320 having an atrial tip electrode 322 and an atrial ring electrode 323 implanted in the atrial appendage. Pacer/ICD 10 is also in electrical communication with the heart by way of a right ventricular lead 330 having, in this embodiment, a ventricular tip electrode 332, a right ventricular ring electrode 334, a right ventricular (RV) coil electrode 336, and a superior vena cava (SVC) coil electrode 338. Typically, the right ventricular lead 330 is transvenously inserted into the heart so as to place the RV coil electrode 336 in the right ventricular apex, and the SVC coil electrode 338 in the superior vena cava. Accordingly, the right ventricular lead is capable of receiving cardiac signals, and delivering stimulation in the form of pacing and shock therapy to the right ventricle.

To sense left atrial and ventricular cardiac signals and to provide left chamber pacing therapy, pacer/ICD 10 is coupled to a "coronary sinus" lead 324 designed for placement in the "coronary sinus region" via the coronary sinus os for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus. Accordingly, an exemplary coronary sinus lead 324 is designed to receive atrial and ventricular cardiac signals and to deliver left ventricular pacing therapy using at least a left ventricular tip electrode 326, left atrial pacing therapy using at least a left atrial ring electrode 327, and shocking therapy using at least a left atrial coil electrode 328. With this configuration, biventricular pacing can be performed. Although only three leads are shown in FIG. 8, it should also be understood that additional stimulation leads (with one or more pacing, sensing and/or shocking electrodes) may be used in order to efficiently and effectively provide pacing stimulation to the left side of the heart or atrial cardioversion and/or defibrillation.

Figure 9:
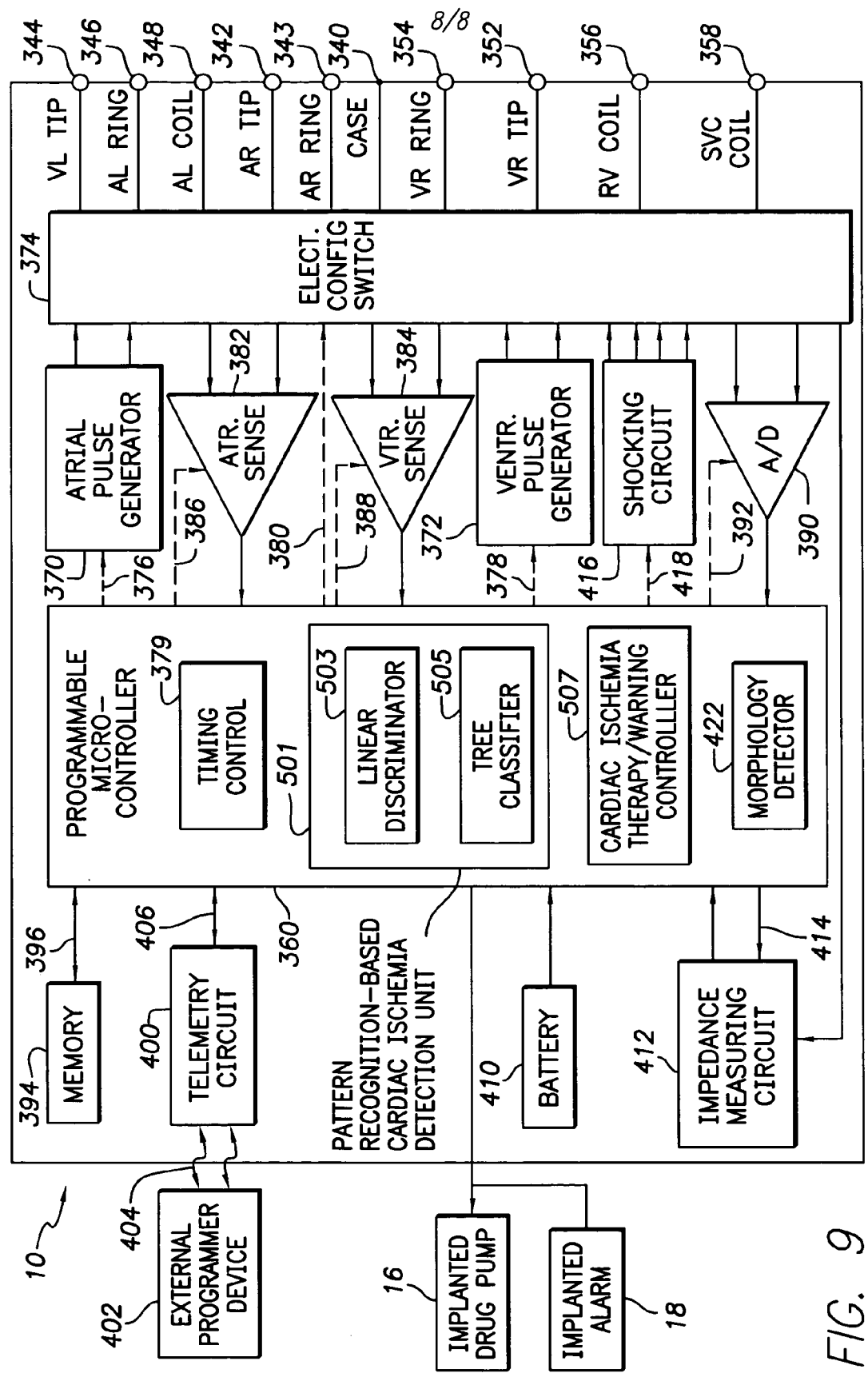
FIG. 9 is a functional block diagram of the pacer/ICD of FIG. 8, illustrating basic circuit elements that provide cardioversion, defibrillation and/or pacing stimulation in the heart and particularly illustrating components for detecting cardiac ischemia and for controlling delivery of therapy or warning signals in response thereto.

A simplified block diagram of internal components of pacer/ICD 10 is shown in FIG. 9. While a particular pacer/ICD is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation as well as providing for the aforementioned apnea detection and therapy. The housing 340 for pacer/ICD 10, shown schematically in FIG. 9, is often referred to as the "can", "case" or "case electrode" and may be programmably selected to act as the return electrode for all "unipolar" modes. The housing 340 may further be used as a return electrode alone or in combination with one or more of the coil electrodes, 328, 336 and 338, for shocking purposes. The housing 340 further includes a connector (not shown) having a plurality of terminals, 342, 343, 344, 346, 348, 352, 354, 356 and 358 (shown schematically and, for convenience, the names of the electrodes to which they are connected are shown next to the terminals). As such, to achieve right atrial sensing and pacing, the connector includes at least a right atrial tip terminal ($A_R$ TIP) 342 adapted for connection to the atrial tip electrode 322 and a right atrial ring ($A_R$ RING) electrode 343 adapted for connection to right atrial ring electrode 323. To achieve left chamber sensing, pacing and shocking, the connector includes at least a left ventricular tip terminal ($V_L$ TIP) 344, a left atrial ring terminal ($A_L$ RING) 346, and a left atrial shocking terminal ($A_L$ COIL) 348, which are adapted for connection to the left ventricular ring electrode 326, the left atrial tip electrode 327, and the left atrial coil electrode 328, respectively. To support right chamber sensing, pacing and shocking, the connector further includes a right ventricular tip terminal ($V_R$ TIP) 352, a right ventricular ring terminal ($V_R$ RING) 354, a right ventricular shocking terminal ($R_V$ COIL) 356, and an SVC shocking terminal (SVC COIL) 358, which are adapted for connection to the right ventricular tip electrode 332, right ventricular ring electrode 334, the RV coil electrode 336, and the SVC coil electrode 338, respectively.

At the core of pacer/ICD 10 is a programmable microcontroller 360, which controls the various modes of stimulation therapy. As is well known in the art, the microcontroller 360 (also referred to herein as a control unit) typically includes a microprocessor, or equivalent control circuitry, designed specifically for controlling the delivery of stimulation therapy and may further include RAM or ROM memory, logic and timing circuitry, state machine circuitry, and I/O circuitry.

Typically, the microcontroller 360 includes the ability to process or monitor input signals (data) as controlled by a program code stored in a designated block of memory. The details of the design and operation of the microcontroller 360 are not critical to the invention. Rather, any suitable microcontroller 360 may be used that carries out the functions described herein. The use of microprocessor-based control circuits for performing timing and data analysis functions are well known in the art.

As shown in FIG. 9, an atrial pulse generator 370 and a ventricular/impedance pulse generator 372 generate pacing stimulation pulses for delivery by the right atrial lead 320, the right ventricular lead 330, and/or the coronary sinus lead 324 via an electrode configuration switch 374. It is understood that in order to provide stimulation therapy in each of the four chambers of the heart, the atrial and ventricular pulse generators, 370 and 372, may include dedicated, independent pulse generators, multiplexed pulse generators or shared pulse generators. The pulse generators, 370 and 372, are controlled by the microcontroller 360 via appropriate control signals, 376 and 378, respectively, to trigger or inhibit the stimulation pulses.

The microcontroller 360 further includes timing control circuitry 379 used to control the timing of such stimulation pulses (e.g., pacing rate, atrio-ventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, etc., which is well known in the art. Switch 374 includes a plurality of switches for connecting the desired electrodes to the appropriate I/O circuits, thereby providing complete electrode programmability. Accordingly, the switch 374, in response to a control signal 380 from the microcontroller 360, determines the polarity of the stimulation pulses (e.g., unipolar, bipolar, combipolar, etc.) by selectively closing the appropriate combination of switches (not shown) as is known in the art.

Atrial sensing circuits 382 and ventricular sensing circuits 384 may also be selectively coupled to the right atrial lead 320, coronary sinus lead 324, and the right ventricular lead 330, through the switch 374 for detecting the presence of cardiac activity in each of the four chambers of the heart. Accordingly, the atrial (ATR. SENSE) and ventricular (VTR. SENSE) sensing circuits, 382 and 384, may include dedicated sense amplifiers, multiplexed amplifiers or shared amplifiers. The switch 374 determines the "sensing polarity" of the cardiac signal by selectively closing the appropriate switches, as is also known in the art. In this way, the clinician may program the sensing polarity independent of the stimulation polarity. Each sensing circuit, 382 and 384, preferably employs one or more low power, precision amplifiers with programmable gain and/or automatic gain control, bandpass filtering, and a threshold detection circuit, as known in the art, to selectively sense the cardiac signal of interest. The automatic gain control enables pacer/ICD 10 to deal effectively with the difficult problem of sensing the low amplitude signal characteristics of atrial or ventricular fibrillation. The outputs of the atrial and ventricular sensing circuits, 382 and 384, are connected to the microcontroller 360 which, in turn, are able to trigger or inhibit the atrial and ventricular pulse generators, 370 and 372, respectively, in a demand fashion in response to the absence or presence of cardiac activity in the appropriate chambers of the heart.

For arrhythmia detection, pacer/ICD 10 utilizes the atrial and ventricular sensing circuits, 382 and 384, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 360 by comparing them to a predefined rate zone limit (i.e., bradycardia, normal, atrial tachycardia, atrial fibrillation, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, antitachycardia pacing, cardioversion shocks or defibrillation shocks).

Cardiac signals are also applied to the inputs of an analog-to-digital (A/D) data acquisition system 390. The data acquisition system 390 is configured to acquire intracardiac electrogram signals, convert the raw analog data into a digital signal, and store the digital signals for later processing and/or telemetric transmission to an external device 402. The data acquisition system 390 is coupled to the right atrial lead 320, the coronary sinus lead 324, and the right ventricular lead 330 through the switch 374 to sample cardiac signals across any pair of desired electrodes. The microcontroller 360 is further coupled to a memory 394 by a suitable data/address bus 396, wherein the programmable operating parameters used by the microcontroller 360 are stored and modified, as required, in order to customize the operation of pacer/ICD 10 to suit the needs of a particular patient. Such operating parameters define, for example, pacing pulse amplitude or magnitude, pulse duration, electrode polarity, rate, sensitivity, automatic features, arrhythmia detection criteria, and the amplitude, waveshape and vector of each shocking pulse to be delivered to the patient's heart within each respective tier of therapy. Other pacing parameters include base rate, rest rate and circadian base rate.

In addition, the stimulation device may be configured to perform Automatic Mode Switching (AMS) wherein the pacemaker reverts from a tracking mode such as a VDD or DDD mode to a nontracking mode such as VVI or DDI mode. VDD, DDD, VVI and DDI are standard device codes that identify the mode of operation of the device. DDD indicates a device that senses and paces in both the atria and the ventricles and is capable of both triggering and inhibiting functions based upon events sensed in the atria and the ventricles. VDD indicates a device that sensed in both the atria and ventricles but only paces in the ventricles. A sensed event on the atrial channel triggers ventricular outputs after a programmable delay, the pacemaker's equivalent of a PR interval. VVI indicates that the device is capable of pacing and sensing only in the ventricles and is only capable of inhibiting the functions based upon events sensed in the ventricles. DDI is identical to DDD except that the device is only capable of inhibiting functions based upon sensed events, rather than triggering functions. As such, the DDI mode is a non-tracking mode precluding its triggering ventricular outputs in response to sensed atrial events. Numerous other device modes of operation are possible, each represented by standard abbreviations of this type.

Advantageously, the operating parameters of the implantable pacer/ICD 10 may be non-invasively programmed into the memory 394 through a telemetry circuit 400 in telemetric communication with the external device 402, such as a programmer, transtelephonic transceiver or a diagnostic system analyzer. The telemetry circuit 400 is activated by the microcontroller by a control signal 406. The telemetry circuit 400 advantageously allows intracardiac electrograms and status information relating to the operation of pacer/ICD 10 (as contained in the microcontroller 360 or memory 394) to be sent to the external device 402 through an established communication link 404. Pacer/ICD 10 further includes an accelerometer or other physiologic sensor 408, commonly referred to as a "rate-responsive" sensor because it is typically used to adjust pacing stimulation rate according to the exercise state of the patient. However, the physiological sensor 408 may further be used to detect changes in cardiac output, changes in the physiological condition of the heart, or diurnal changes in activity (e.g., detecting sleep and wake states) and to detect arousal from sleep. Accordingly, the microcontroller 360 responds by adjusting the various pacing parameters (such as rate, AV Delay, V-V Delay, etc.) at which the atrial and ventricular pulse generators, 370 and 372, generate stimulation pulses. While shown as being included within pacer/ICD 10, it is to be understood that the physiologic sensor 408 may also be external to pacer/ICD 10, yet still be implanted within or carried by the patient. A common type of rate responsive sensor is an activity sensor incorporating an accelerometer or a piezoelectric crystal, which is mounted within the housing 340 of pacer/ICD 10. Other types of physiologic sensors are also known, for example, sensors that sense the oxygen content of blood, respiration rate and/or minute ventilation, pH of blood, ventricular gradient, etc.

The pacer/ICD additionally includes at least one battery 410 of other power source, which provides operating power to all of the circuits shown in FIG. 9. The battery 410 may vary depending on the capabilities of pacer/ICD 10. If the system only provides low voltage therapy, a lithium iodine or lithium copper fluoride cell may be utilized. For pacer/ICD 10, which employs shocking therapy, the battery 410 must be capable of operating at low current drains for long periods, and then be capable of providing high-current pulses (for capacitor charging) when the patient requires a shock pulse. The battery 410 must also have a predictable discharge characteristic so that elective replacement time can be detected. Accordingly, pacer/ICD 10 is preferably capable of high voltage therapy and appropriate batteries.

As further shown in FIG. 9, pacer/ICD 10 includes an impedance measuring circuit 412 that is enabled by the microcontroller 360 via a control signal 414. Uses for an impedance measuring circuit include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 412 is advantageously coupled to the switch 74 so that any desired electrode may be used.

In the case where pacer/ICD 10 is intended to operate as an implantable cardioverter/defibrillator (ICD) device, it detects the occurrence of an arrhythmia, and automatically applies an appropriate electrical shock therapy to the heart aimed at terminating the detected arrhythmia. To this end, the microcontroller 360 further controls a shocking circuit 416 by way of a control signal 418. The shocking circuit 416 generates shocking pulses of low (up to 0.5 joules), moderate (0.5-10 joules) or high energy (11 to 40 joules), as controlled by the microcontroller 360. Such shocking pulses are applied to the heart of the patient through at least two shocking electrodes, and as shown in this embodiment, selected from the left atrial coil electrode 328, the RV coil electrode 336, and/or the SVC coil electrode 338. The housing 340 may act as an active electrode in combination with the RV electrode 336, or as part of a split electrical vector using the SVC coil electrode 338 or the left atrial coil electrode 328 (i.e., using the RV electrode as a common electrode). Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5-40 joules), delivered asynchronously (since R-waves may be too disorganized), and pertaining exclusively to the treatment of fibrillation. Accordingly, the microcontroller 360 is capable of controlling the synchronous or asynchronous delivery of the shocking pulses.

Microcontroller 360 also includes various components directed to the detecting cardiac ischemia via pattern recognition and for controlling delivery of therapy and warnings in response thereto. In particular, the pacer/ICD includes a pattern recognition-based cardiac ischemia detection unit 501 that detects episodes of cardiac ischemia in the patient based in accordance with the techniques described above. Ischemia detection unit 501 includes either a linear discriminator 503 or a tree classifier 505, or both. (If both, the detection system preferably detects ischemia only if both the linear discriminator and the tree classifier output "ischemic" signals.) A cardiac ischemia therapy/warning controller 507 controls delivery of therapy and/or warning signals in response to the detection of cardiac ischemia, again in accordance with techniques already described.

Depending upon the implementation, the various components of the microcontroller may be implemented as separate software modules or the modules may be combined to permit a single module to perform multiple functions. In addition, although shown as being components of the microcontroller, some or all of these components may be implemented separately from the microcontroller, as hardware devices.

In general, a wide variety of techniques can be implemented consistent with the principles the invention and no attempt is made herein to describe all possible techniques. Although described primarily with reference to an example wherein the implanted device is a pacer/ICD, principles of the invention are applicable to other implantable medical devices as well. In addition, whereas the techniques described herein are performed by the implanted device, the techniques may alternatively be performed by an external device using IEGM signals or other signals transmitted from the implanted device. For example, a bedside monitor may be configured to receive IEGM signals from the implanted device via "long-range" telemetry then analyze the signals using the aforementioned techniques and issue any appropriate warnings. Alternatively, the bedside monitor may transmit the IEGM data to a central server or other central processing device, which analyzes data from multiple patients to detect ischemia within any of those patients. In such an implementation, the central processing device then transmits appropriate warning signals to the bedside monitor of the patient for warning the patient and additionally transmits appropriate warning signals to the physician associated with the patient or a third party such as emergency medical service (EMS) personnel.

The various functional components of the exemplary systems described herein may be implemented using any appropriate technology including, for example, microprocessors running software programs or application specific integrated circuits (ASICs) executing hard-wired logic operations. The exemplary embodiments of the invention described herein are merely illustrative of the invention and should not be construed as limiting the scope of the invention. Note also that the term "including" as used herein is intended to be inclusive, i.e. "including but not limited to."

What is claimed is:

1. A method for use with an implantable medical device for detecting cardiac ischemia in a patient in which the device is implanted, comprising:

detecting a plurality of values representative of different morphological features of electrical cardiac signals, including ST segment parameters and one or both of atrial depolarization morphological parameters and ventricular depolarization morphological parameters; and detecting whether the patient is subject to an on-going episode of cardiac ischemia by applying the plurality of values to a pattern classifier configured to identify patterns representative of cardiac ischemia.

2. The method of claim 1 wherein the atrial depolarization morphological parameters applied to the pattern classifier include one or more of atrial depolarization event duration, atrial depolarization event slope, and atrial depolarization event amplitude.

3. The method of claim 1 wherein the ventricular depolarization morphological parameters applied to the pattern classifier include one or more of ventricular depolarization event duration, ventricular depolarization event slope, and ventricular depolarization event amplitude.

4. The method of claim 1 wherein the pattern classifier is a linear discriminant-based pattern classifier and wherein detecting whether the patient is subject to an on-going episode of cardiac ischemia comprises:

applying the values to the linear discriminant-based pattern classifier to generate a classification metric;

comparing the classification metric to a threshold representative of cardiac ischemia; and generating a signal indicative of the detection of cardiac ischemia if the classification metric exceeds the threshold.

5. The method of claim 1 wherein the pattern classifier is a classification tree-based pattern classifier and wherein detecting whether the patient is subject to an on-going episode of cardiac ischemia comprises:

applying the values to the classification tree to classify the values as either being representative of cardiac ischemia or not being representative of cardiac ischemia; and generating a signal indicative of the detection of cardiac ischemia if the classification tree classifies the values as being representative of cardiac ischemia.

6. The method of claim 1 wherein detecting whether the patient is subject to an on-going episode of cardiac ischemia is performed substantially in real-time by applying values representative of morphological features of a latest heartbeat of the patient to the pattern classifier.

7. The method of claim 1 wherein detecting whether the patient is subject to an on-going episode of cardiac ischemia is performed periodically by applying values representative of morphological features of a plurality of recent heartbeats of the patient to the pattern classifier.

8. The method of claim 1 further comprising training the pattern classifier to recognize cardiac ischemia based on morphological features of electrical cardiac signals associated with cardiac ischemia.

9. The method of claim 1 further comprising delivering therapy in response to the detection of an episode of cardiac ischemia.

10. The method of claim 9 wherein an implantable drug pump is provided and wherein the step of delivering therapy in response to the detection of an episode of cardiac ischemia includes the step of delivering anti-thrombolytic medications to the patient using the drug pump.

11. The method of claim 9 wherein an implantable cardiac stimulation device is provided and wherein the step of delivering therapy in response to the detection of an episode of cardiac ischemia includes the step of delivering pacing therapy at a reduced pacing rate.

12. The method of claim 1 further comprising generating a warning signal in response to detection of an episode of cardiac ischemia.

13. The method of claim 1 wherein the parameters detected and applied to the pattern classifier include an atrioventricular (AV) interval.

14. The method of claim 1 wherein the implantable medical device includes an implantable cardiac defibrillation device provided with defibrillation shock capacitors and wherein the capacitors are charged in response to the detection of an episode of cardiac ischemia.

15. A system for use with an implantable medical device for detecting cardiac ischemia in a patient in which the device is implanted, comprising:
- a detection unit operative to detect a plurality of values representative of different morphological features of electrical cardiac signals, including ST segment parameters and one or both of atrial depolarization morphological parameters and ventricular depolarization morphological parameters; and
- a pattern recognition-based cardiac ischemia detection unit operative to detect whether the patient is subject to an on-going episode of cardiac ischemia by applying the plurality of values to a pattern classifier configured to identify patterns representative of cardiac ischemia.

16. The system of claim 15 wherein the pattern recognition-based cardiac ischemia detection unit is operative to analyze one or more of: atrial depolarization event duration, atrial depolarization event slope, and atrial depolarization event amplitude.

17. The system of claim 15 wherein the pattern recognition-based cardiac ischemia detection unit is operative to analyze one or more of: ventricular depolarization event duration, ventricular depolarization event slope, and ventricular depolarization event amplitude.

18. A system for use with an implantable medical device for detecting cardiac ischemia in a patient in which the device is implanted, comprising:
- means for detecting a plurality of values representative of different morphological features of electrical cardiac signals, including ST segment parameters and one or both of atrial depolarization morphological parameters and ventricular depolarization morphological parameters;
- means for detecting whether the patient is subject to an on-going episode of cardiac ischemia by applying the plurality of values to a pattern classifier configured to identify patterns representative of cardiac ischemia; and
- means for delivering therapy in response to the detection of an episode of cardiac ischemia.

19. The system of claim 18 wherein the means for detecting whether the patient is subject to an on-going episode of cardiac ischemia comprises means for analyzing one or more of atrial depolarization event duration, atrial depolarization event slope, and atrial depolarization event amplitude in conjunction with ST segment parameters.

20. The system of claim 18 wherein the means for detecting whether the patient is subject to an on-going episode of cardiac ischemia comprises means for analyzing one or more of ventricular depolarization event duration, ventricular depolarization event slope, and ventricular depolarization event amplitude in conjunction with ST segment parameters.

* * * * *

UNITED STATES PATENT AND TRADEMARK OFFICE
CERTIFICATE OF CORRECTION

PATENT NO. : 7,610,086 B1  Page 1 of 1
APPLICATION NO. : 11/394724
DATED : October 27, 2009
INVENTOR(S) : Ke et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 853 days.

Signed and Sealed this

Twelfth Day of October, 2010

David J. Kappos
*Director of the United States Patent and Trademark Office*